United States Patent [19]

Yang

[11] Patent Number: 5,260,191
[45] Date of Patent: Nov. 9, 1993

[54] METHOD FOR DIAGNOSING TUMORS

[75] Inventor: Ning-Sun Yang, Verona, Wis.

[73] Assignee: Agracetus, Inc., Middleton, Wis.

[21] Appl. No.: 828,087

[22] Filed: Jan. 30, 1992

[51] Int. Cl.$^5$ .......................... C12Q 1/68; G01N 33/48
[52] U.S. Cl. ........ ................................... 435/6; 436/63; 436/64; 436/86
[58] Field of Search ...................... 435/6, 69.1; 436/63, 436/64, 86

[56] References Cited

U.S. PATENT DOCUMENTS

| | | | |
|---|---|---|---|
| 4,945,050 | 7/1990 | Sanford et al. | 435/172.1 |
| 5,015,580 | 5/1991 | Christou et al. | 435/172.3 |

FOREIGN PATENT DOCUMENTS

WO9100359  1/1991  PCT Int'l Appl. .

OTHER PUBLICATIONS

Freifelder (1987), Molecular Biology, 2nd Ed., (Jones & Bartlett Publishers, Boston) p. 792.

Marx, J. "Possible New Cancer Gene Found," *Science*, p. 1317 (Mar. 15, 1991).
Marx (1989), Science 246:1386–1388.

*Primary Examiner*—Richard A. Schwartz
*Assistant Examiner*—Philip W. Carter
*Attorney, Agent, or Firm*—Quarles & Brady

[57] ABSTRACT

A method for determining the developmental stage of a tumor is disclosed. The method comprises the steps of isolating tumor cells, dividing the cells into two samples, transducing one sample with a reporter gene, transducing the other sample with both a reporter gene and a staging gene (wherein the staging gene corresponds to a gene that is differentially expressed in neoplastic and normal cells and is chosen by its ability to be predictive of a certain stage of neoplastic development), analyzing both samples for the level of expression of the reporter gene and comparing the expression level in the samples. In a particularly advantageous embodiment of the invention, the staging gene is JR-ras and the reporter gene is lux.

6 Claims, 6 Drawing Sheets

TUMOR PROGRESSION OR UNCONTROLLED CELL GROWTH

NORMAL COLON CELL
↓ Chromosome 5 Gene (APC)

INCREASED CELL GROWTH
↓

ADENOMA I
↓ DNA Loses Methyl Groups

RAS Gene Mutation

ADENOMA II
↓ Chromosome 18 Loss - DCC Gene

ADENOMA III
↓ Chromosome 17 Loss - p53 Gene

CARCINOMA
↓ Other Chromosome Losses

METASTASIS

Restriction sites: H, BamHI; X, XhoI; K, KpnI; E, EcoRI

Structural Features: LTR, MuLV-LTR; v-Ha-ras, mutated ras gene; SV40, SV40 promoter; Neo, NeoR gene; pBRori, origin of replication; Am$^r$, Am$^r$ gene marker; SD, splice donor; SA, splice acceptor; TAG, amber mutation in the initiation codon of p160.

This pJR-ras gene clone is as described by B. Wang et al. (Cancer Research, 51:2642, 1991)

FIG. 5

- The p53 clone is as described by Chen et al. in Science, 250:1576, (1990).

- The MuLV-LTR promoter/enhancer drives the p53 gene

FIG. 6

METHOD FOR DIAGNOSING TUMORS

FIELD OF THE INVENTION

The present invention relates to methods of diagnosing the developmental stage of a tumor. More specifically, the invention relates to the staging of a tumor by examining the expression level of foreign genes inserted in tumor cells.

BACKGROUND OF THE INVENTION

Figure 1:
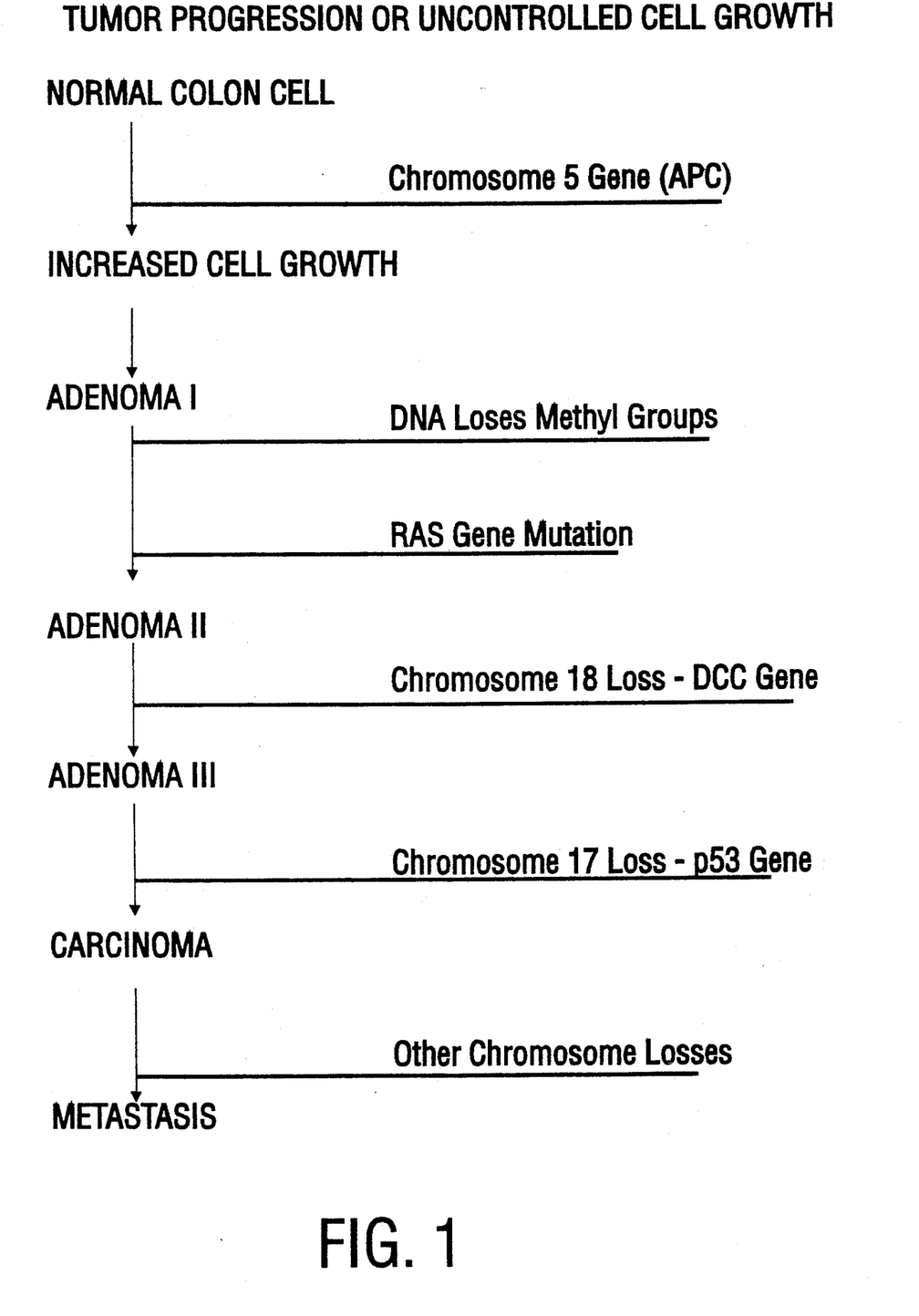
FIG. 1 is a diagram of the developmental stages of colon cancer correlated with mutations of oncogenes and tumor suppressor genes.

Neoplastic transformation of normal cells into malignant tumor cells and metastatic cancer cells proceeds in a series of progressive stages. Recent molecular biological studies of tumor progression provide evidence suggesting that mutation, activation or loss of specific genes (namely proto-oncogenes, oncogenes and tumor suppressor genes) are carried out in a specific orderly sequence which correlates well with tumor progression in colon tissues (Kingler and Vogelstein, *Science* 251: 1366 1991), and presumably so for most other types of cancer, such as breast tumors. A typical example for certain colon tumors has been described by B. Vogelstein, and is illustrated in FIG. 1. FIG. 1, taken from Kingler and Vogelstein (supra, 1991), diagrams the series of mutations that correspond to a series of gene mutation, expression or suppression steps which characterize the progression of colon cancer. For example, the ras gene is mutated in an early step. In a later step, the P53 gene is lost or mutated. Thus, human cancers are now evaluated and characterized as a developmental genetic disease, and steps in the progression of the disease may be characterized and distinguished at a molecular level.

At present, clinical diagnosis of tumor stage usually involves detection of histological markers that operationally define benign, adenoma, carcinoma, infiltrating carcinoma and metastatic carcinoma cells. In many cases, this morphological diagnosis is known to be insufficient or misleading for prognosis and treatment of cancer patients. Molecular genetic probes and tools could be used to characterize the biochemical and molecular phenotype of tumors at different stages. This genetic information would be useful to fine-tune the identification of tumor stages and, thus, would be useful for prognosis and treatment of specific tumors. Due to the small size of early-stage tumors or other suspect tissues, it may be difficult to use direct biochemical analysis to test for molecular phenotypes.

The prior art lacks a method to characterize and stage a patient's clinical tumor sample with a reporter gene expression assay system.

SUMMARY OF THE INVENTION

The method of the present invention is a method intended to help determine the developmental stage of a tumor. Tumor cells are isolated and divided into first and second samples. The first sample is transduced with a reporter gene and the second sample is transduced with both a reporter gene and a staging gene. The staging gene is a gene known to have a differential mode of expression in normal and neoplastic cells. The staging gene is chosen to be predictive of a certain stage of neoplastic development. The level of expression of the reporter gene is determined in both samples and compared. The level of expression of the reporter gene in neoplastic or malignant cells will be different from that in non-neoplastic or normal, benign cells.

In an advantageous embodiment of the invention, the staging gene is either an oncogene or a tumor suppressor gene.

In a particularly advantageous embodiment of the present invention, the staging gene is JR-ras or p53 and the reporter gene is CMV-lux.

The object of the present invention is to provide a convenient and accurate assay for the developmental stage of neoplastic cells.

An advantage of the present invention is that neoplastic cells may be more accurately staged for diagnostic and treatment purposes.

Another advantage is that the assay may be quickly done, thus promoting rapid characterization of cancers and rapid choice of therapeutic alternatives.

Other objects, advantages and features of the present invention will become apparent from the following specification taken in conjunction with the drawings.

BRIEF DESCRIPTION OF THE PREFERRED EMBODIMENT

A. In General

Oncogene and tumor suppressor genes are now known to encode key proteins or growth factors which regulate cell growth, differentiation and de-differentiation. Consecutive and orderly genetic changes of these oncogenes or tumor suppressor genes (mutation, activation or chromosome loss) are responsible for the progression of normal cells into neoplastic and malignant states and for tumor progression from one stage to the next. The modified expression of involved oncogenes or tumor suppressor genes also influences the expression of other cellular genes.

We have found, as shown below in the Examples, that a reporter gene assay system can differentiate normal cells from neoplastic or malignant cells by taking advantage of this change of expression of cellular genes. In this system, tumor cells or other cells to be tested are transduced with a reporter gene and with a specific gene, such as ras, which has been identified as being differentially expressed in normal and neoplastic cells. By "neoplastic cells" we mean cells that are experiencing an abnormal or uncontrolled proliferation. These cells may be either benign or malignant. By "neoplastic development" we mean the various stages of progression of cell development from normal cells to cancerous, metastatic cells. We call the specific oncogene or tumor suppressor gene used to test for neoplastic character or stage a "staging" gene. A suitable staging gene is one known to exhibit a differential mode of expression in neoplastic and normal cells. By "differential mode of expression" we mean that the structure or expression of the staging gene is different in the neoplastic cell compared to a normal cell. For instance, the staging gene could be mutated or altered or could be over- or under-expressed in the neoplastic cell.

We found that transduction of normal cell cultures with a ras oncogene staging gene and a reporter gene results in either repression or, at most, maintenance of the level of reporter gene expression in the transgenic cells. By contrast, cotransformation of the same staging oncogene and the same reporter gene DNA in neoplastic or immortalized cells, results in a 1.5 to 4-fold increase in reporter gene expression.

Therefore, stimulation of reporter gene expression by transfection with the staging gene in neoplastic or immortalized cells, and the lack of stimulation of expression in normal cells, can be used as an index for indicating the presence of a genetic mutation in tumor cells that is "earlier" than the staging gene mutation (e.g., successful use of ras as a staging gene would indicate that the APC gene mutation had occurred in colon tumor cells, see pathway described in FIG. 1), and for indicating the lack of this mutation in normal cells. This assay works because the presence or absence of the APC gene mutation controls the level or effect of ras gene expression in normal cells compared to ras gene expression in neoplastic or progressing tumor cells. This difference in ras expression has a similar effect on reporter gene expression. The difference in reporter gene expression can serve as a marker, to distinguish the different genetic and physiological make-up existing between normal and malignant cells (e.g., APC gene mutation). In essence, the test reveals the biochemical phenotype of the tested cells. The assay system thus provides a diagnostic test for identification of the presence or absence of oncogene mutations or tumor suppression gene mutation(s) that precede mutation of the staging gene (i.e., ras, in this case) in the tumorigenesis pathway. For an "unknown" tumor or "unknown" cells of an individual patient, absence of such ras-mediated reporter gene activation would indicate a benign tumor or benign cells. Reporter gene activation would indicate a malignancy, such as adenocarcinoma. Similar test assays can be used for other cells or tissues suspected of neoplasm or malignancy.

The use of the ras gene in a cotransduction (co-transfer of genes as plasmid DNA clones) experiment with the CMV-lux reporter gene is only one example of the many possible staging gene and reporter gene combinations. Similarly, one can use a tumor suppressor gene, such as p53, for downstream (i.e., toward metastasis) analysis among various colon tumor or cancer cells. In the colon cancer system, use of the p53 gene as a staging gene would be useful to identify ras gene mutation(s) in the colon cell, since the ras gene mutation precedes the p53 gene mutation in colon cell tumorigenesis.

Figure 2:
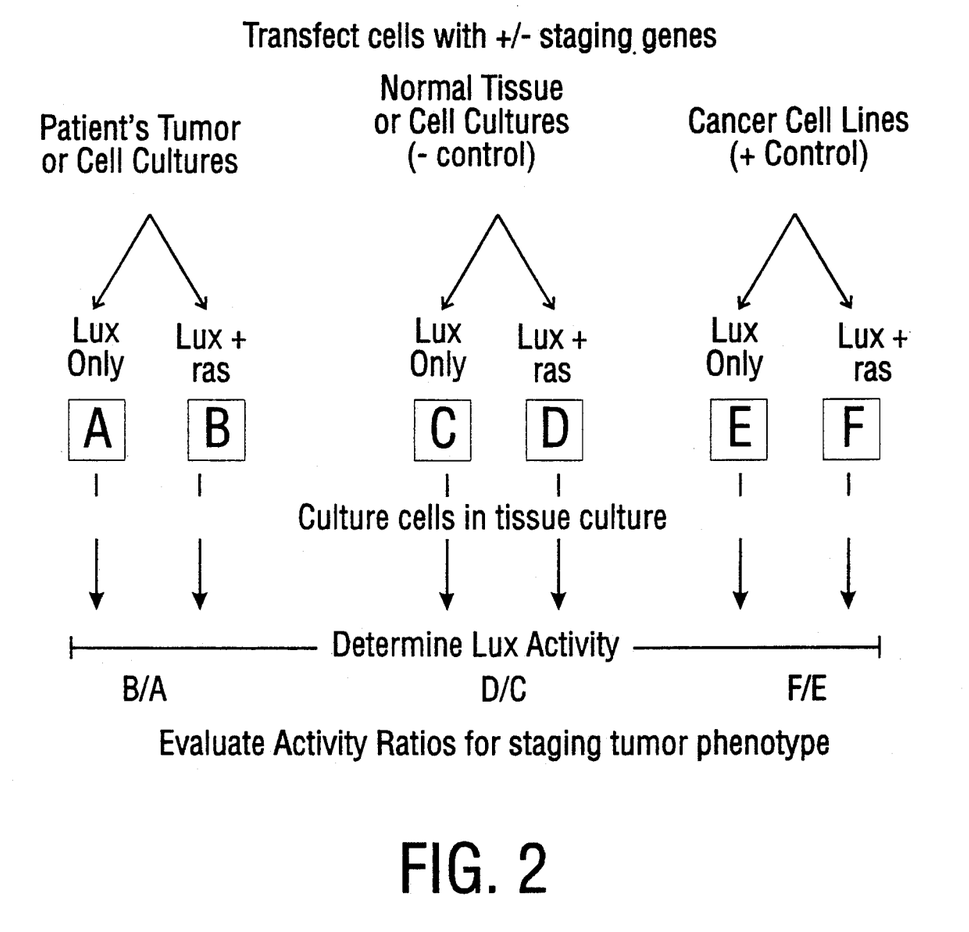
FIG. 2 is a flow chart representation of the assay of the present invention.

The idealized reporter gene assay system in accordance with the present method follows a basic design. A flow chart representation of the steps of this assay is diagramed in FIG. 2. A tumor sample is isolated from the patient and prepared for gene transfer. The sample is then divided into two samples (A and B). Sample A is transduced with a reporter gene, such as CMV-lux. Sample B is transduced with the reporter gene and with a staging gene. The level of the expression of the reporter gene is then determined, and the level of the reporter gene expression is compared between samples A and B. A parallel procedure is also followed for both negative and positive controls. A B/A ratio of one or less than one is indicative of a normal cell. A B/A ratio of approximately 1.5 or greater is indicative of a neoplastic character.

A combination of reporter gene assays using different oncogene or tumor suppressor genes in cotransduction tests could be used to identify the current stage of a specific tumor sampled from an individual patient.

B. System Design and Procedures for Diagnosis of Tumor Stage

1. Physical components for the assay system.

The assay first requires a sample of the tumor or other tissue to be analyzed. This sample may be part of a solid tumor, but any mammalian somatic cells capable of gene transfer are suitable. A portion of the solid tumor may be removed and used to establish a primary culture in a Petri dish, using appropriate growth medium. Alternatively, short term organ culture may be established from a tumor slice or other slice of organ tissue. If one wishes to assay cells, such as bone marrow cells, these cells may be removed from the patient and cultured in appropriate medium.

Both a negative and positive control are useful in this assay. These are samples C, D, E and F in FIG. 2. As FIG. 2 indicates, both negative and positive control samples will be split into two samples, half to be transduced with the reporter gene (samples C and E) and half with both the reporter gene and the staging gene (samples D and F).

A preferably negative control is a normal tissue sample of the same type as the tumor tissue. Preferably, comparable cultures for normal and tumor cells or tissues are used, e.g. one day old primary cell cultures. These cells are cultured in appropriate media. As a negative control, normal tissues may be surgically removed along with the tumor explants, and used to establish a primary cell culture or organ culture. Known normal biopsy or autopsy tissues from appropriate donors may also be used. Additionally, short-term stock human cell cultures, available from biological supply houses such as ATCC, may be used as a negative control. Cancer cell lines, available from ATCC and other suppliers, may be used as a positive control. One example of such a positive control is MCF-7, an established human cancer cell line.

Figure 3:
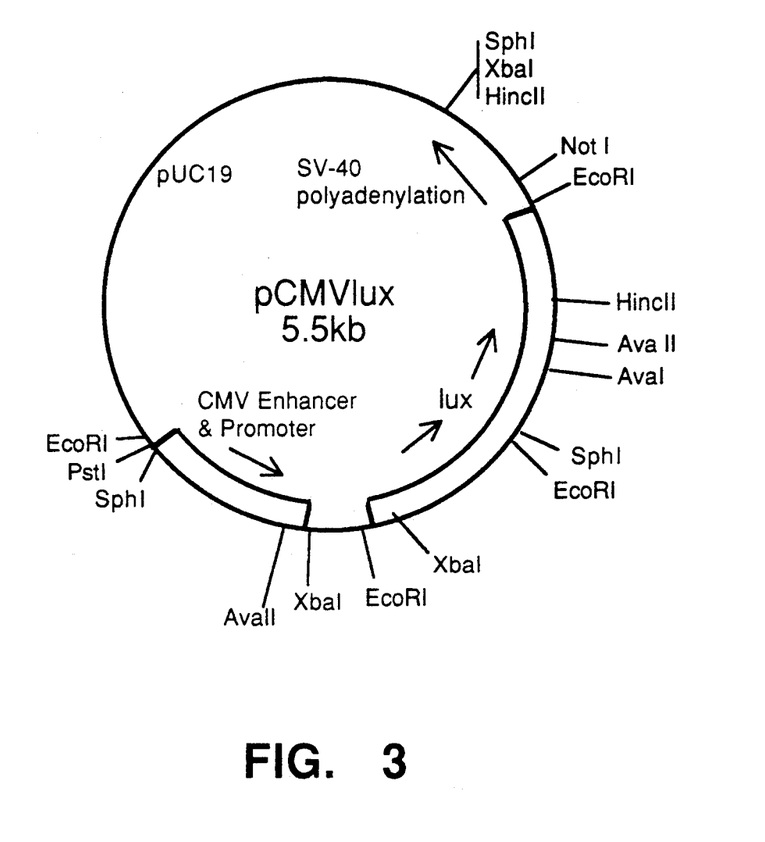
FIG. 3 is a restriction site map of plasmid CMV-lux.
Figure 4:
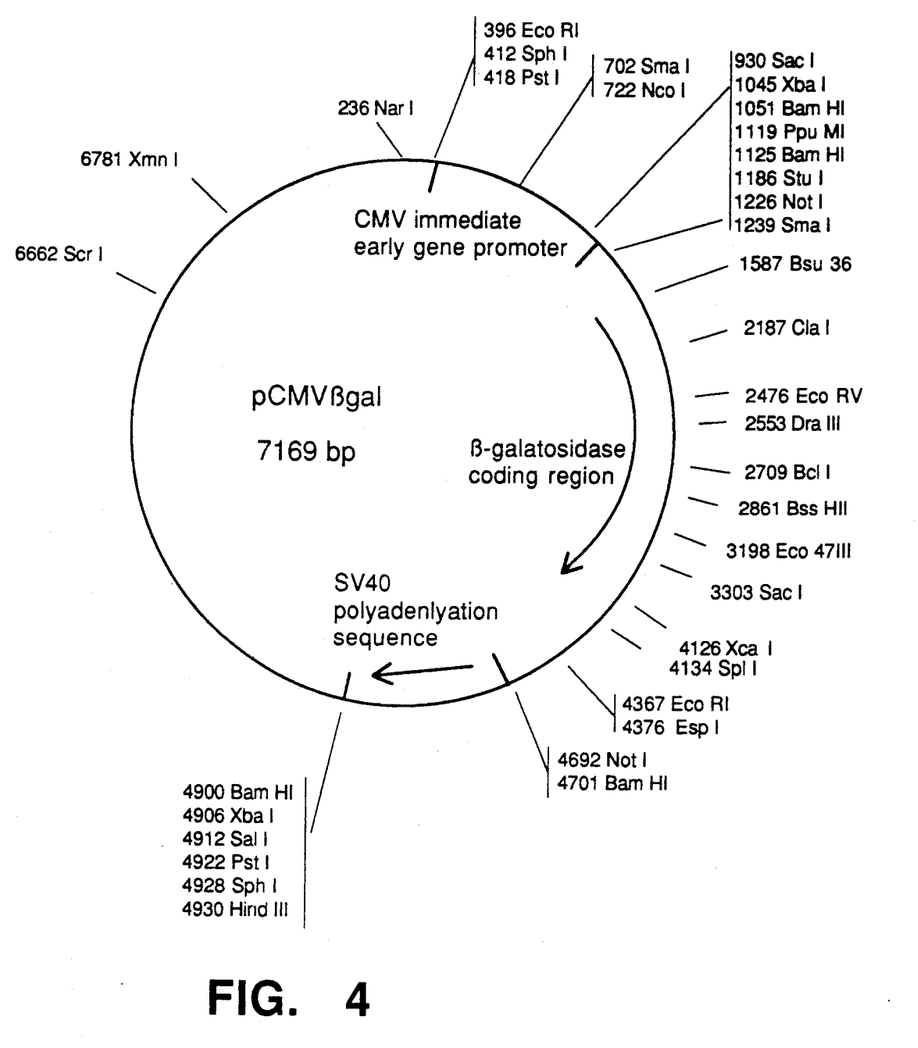
FIG. 4 is a restriction site map of plasmid CMV-gal.

A reporter gene is also needed to gauge the presence of enhanced cell response. Such a gene needs to be linked to a promoter capable of expression in the presence of a staging gene. Two examples of such a construction are diagramed in FIGS. 3 and 4. FIG. 3 is a restriction map of a plasmid containing both the CMV (cytomegalovirus intermediate early) promoter and the luciferase or lux gene. The lux gene encodes the enzyme luciferase, the luminescent product of which may be assayed via a luminometer. FIG. 4 is a restriction diagram of a plasmid encoding the CMV promoter and the beta-galactosidase gene. Expression of the beta-galactosidase which may be assayed by convenient colorimetric assay using a substrate such as X-gal. Many other combinations of promoter and reporter genes are possible. For instance, the CMV promoter may be replaced with the SV-40 (simian virus-40) or the RSV (Rouse sarcoma virus) promoters, both of which are widely used for mammalian gene transfer experiments. The lux gene may be replaced with the CAT (chloramphenicol transferase) gene.

Figure 5:
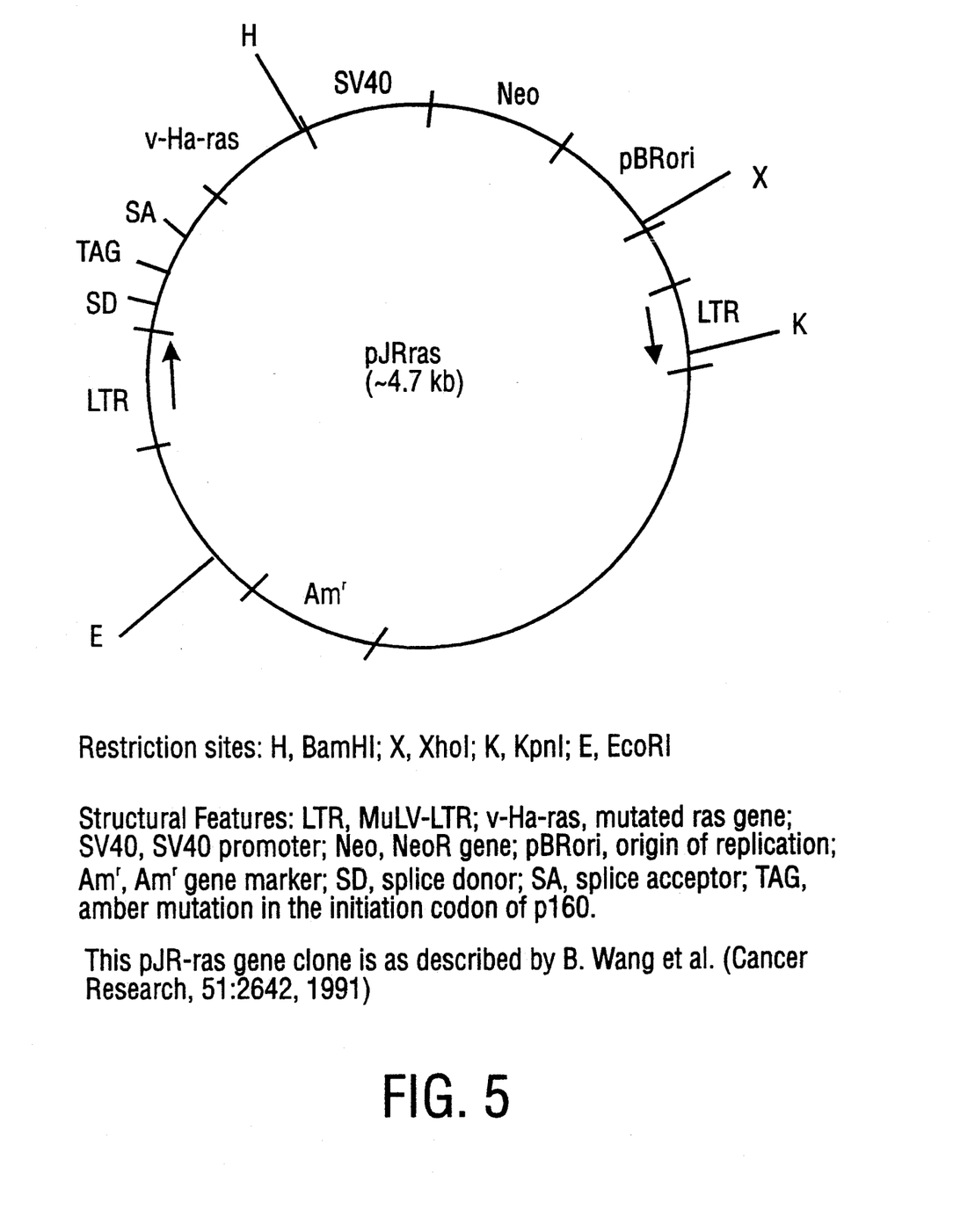
FIG. 5 is a restriction site map of a plasmid containing JR-ras.
Figure 6:
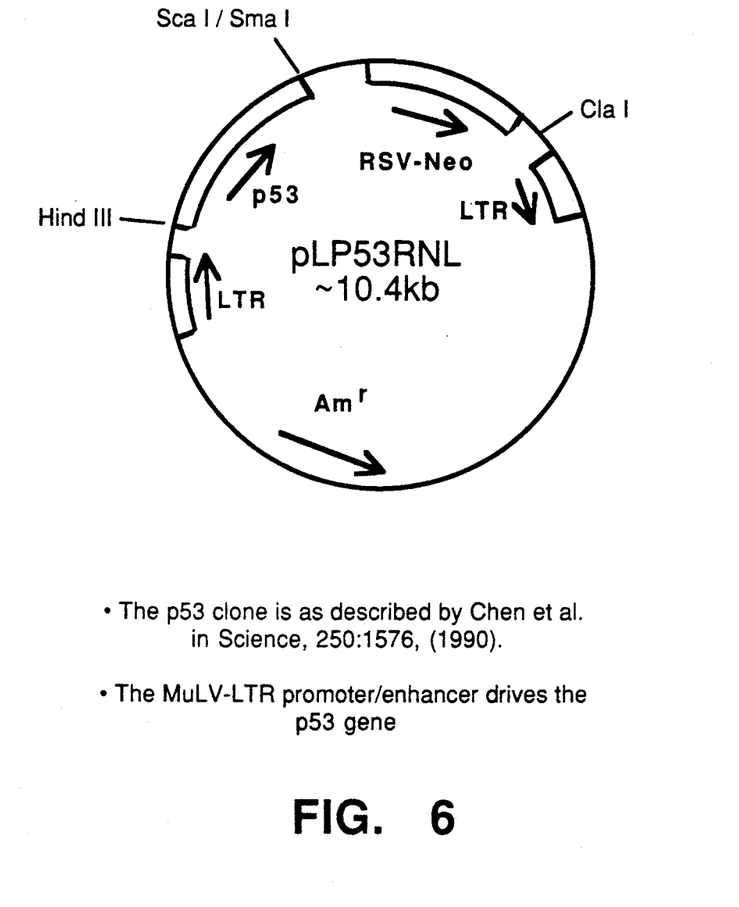
FIG. 6 is a restriction site map of a plasmid containing p53.

The system requires co-transfer of the reporter gene with a staging gene. The ras gene (JR-ras) and the p53 gene are examples of suitable staging genes. Suitable ras and p53 genes may be obtained from American Type Culture Collection (ATCC) Catalogue of Recombinant DNA Materials, a construction may be created where transcription of the ras or p53 gene is controlled by the MuLV-LTR promoter/enhancer. We obtained a plasmid, described at FIG. 5, containing the JR-ras gene from Dr. Michael M. Gould, University of Wisconsin. A plasmid containing a suitable p53 gene is described by P. L. Chen et al. (*Science* 250:1576, 1990) and is diagramed in FIG. 6.

The ras gene is endogenous to mammalian cells and is found in altered or mutated forms in cancer cells. This scenario is generally true for all oncogenes and tumor suppressor genes. It is important that the mutated form (e.g. V-Ha-ras) of the staging gene be used in the assay of the present invention, for it is the mutant form that will activate the reporter gene, along with other cellular genes.

Another specific example of a suitable staging gene is the p53 tumor suppressor gene. A mutated p53 gene or over-production of normal p53 gene can both cause tumor progression. There are other oncogene and tumor suppressor genes that would be useful in the present assay. The staging gene is chosen by its participation in a certain stage of tumorigenesis in a specific tissue type. As the mutation pathway of other tumors becomes known, other oncogenes and tumor suppressor genes that become mutated in the tumorigenesis process may be chosen for incorporation in this assay.

In the examples below, the staging gene and the reporter gene are on two separate vectors. It is also possible that the genes could both be on the same vector.

C. Design and Procedure for Gene Transfer and Expression Assays

To perform this assay, a method of inserting the reporter gene and staging gene into the cells to be tested is necessary. One suitable gene transfer method is based on the bombarding of the cells to be transduced with very small carrier particles that are coated with DNA. This gene transfer technique has been widely used on a variety of plant and animal tissues. U.S. Pat. No. 4,945,050 describes broadly the technique, and U.S. Pat. No. 5,015,580 describes the use of the technique to genetically engineer soybean and also describes an apparatus which was used in the examples below. Published PTC Patent Application No. W091/00359 also describes this style of particle acceleration apparatus and its applicability to the transduction of animal somatic cells. Another style of apparatus for performing particle mediated transduction is commercially available from Bio-Rad Laboratories. While other techniques for gene transfer adaptable for use with mammalian cells, such as retrovirus vectors and liposome transfer, may also be used in the present process, the accelerated particle approach is most conveniently used. This procedure is further described in the Examples below. The transduction system must provide at least transient gene expression. By "transduction" we mean an insertion of foreign genetic material into a cell, and the expression of that foreign genetic material. This change may be permanent or transient.

The next step of the assay is to allow the transgenic cultures to grow in appropriate culture medium, and then to examine the level of reporter gene activity in the replicate cultures. An activity ratio of the reporter gene is determined for A and B samples, C and D samples, and E and F samples. The B/A level is compared to the D/C and F/E. A test tumor sample with a B/A ratio similar to D/C, but not F/E, indicates a benign nature of the test tumor. A B/A ratio similar to F/E, but not D/C, indicates a malignant nature. In the FIG. 2 example, the B/A ratio is similar to the F/E ratio. This indicates that the test tumor sample has a complete tumorigenesis progression of up to ras gene activation stage. In our experiments, we determined that a B/A ratio of greater than approximately 1.5 was a positive result.

EXAMPLES

1. IN GENERAL

A. Processing of Tumor Samples from Individual Patients

Solid tumor specimens were embedded into low temp. melting agar solution. The agar was solidified at 4° C. Thin (50 to 100μ) tumor tissue sections were obtained using a vibratome sectioning device. Consecutive, viable tumor sections were immediately submerged into appropriate culture medium, and then cultivated in an organ culturefloating mode.

Alternatively or additionally, tumor specimens were enzymatically digested into cell aggregates, and plated to generate replicate primary cultures in a collagen gel culture system, which has worked effectively for both normal and malignant human breast tissues.

B. Processing of Cells and Cell Lines

Epithelial cells were isolated from the mammary tissues of 2 month-old female rats, and purified as mammary organids by enzymatic digestion and physical means of tissue separation as described by Kirkland et al. (J. Natl. Cancer Inst. 63, 29–41, 1979).

Various cell lines (NIH/3T3, CHO, MCF-7, HEPG2) and purified rat epithelial cells were plated into 35 mm tissue culture dishes using the appropriate media, containing serum supplement and growth factors as suggested by the catalogue and handbook of cell supplier (ATCC, *Cell Lines and Hybridomas*, 6th edition, 1988). Cell cultures were grown to $\approx 80\%$ confluency for 3 to 4 days.

C. Transfer of Stacing Gene and Reporter Gene into Cells by the Accelerated Microproiectile Method Tumor sections or primary cultures, cells and cell lines were transduced by standard accelerated microprojectile methods. This method and an apparatus useful for performing this gene transfer is disclosed in U.S. Pat. No. 5,015,580. (The description of the particle acceleration device in this patent is hereby incorporated by reference.) The standard transduction conditions that we used in the examples below was as follows: Cells or tissues were placed on a 35 mm Petri dish. The samples were bombarded with 1-3 μgold carrier particles coated with plasmid DNA at either 1 μg CMV-lux DNA per mg particles or 1 μg CMV-lux DNA and 1 μg JR-ras DNA per mg particles. Plasmid DNA was purified by standard methods.

The procedure for coating the carrier particles was as follows: 10 mg gold beads and 2.5 μg of each plasmid DNA were added to 100 μl H$_2$O. This suspension was added slowly to a solution containing 12.5% PEG and 0.2M CaCl$_2$ to precipitate the DNA onto the beads. The beads were sedimented, rinsed once with 100% ethanol and then resuspended in 10 ml of 100% ethanol. This 10 ml is our stock solution. We swirled the solution to mix it, and withdrew 364 μl to load onto the carrier sheet. The particles were loaded onto the carrier sheet at a rate of 0.1 mg beads/cm$^2$. The voltage used to propel the coated carrier particles was 7 kilovolts.

The plasmids used in the Examples are as described in FIGS. 3, 4, 5, and 6. The p53-containing plasmid was obtained from Dr. W. H. Lee (San Antonio, University of Texas) and is described in *Science* 250:1576, 1990.

D. Transient Gene Expression Assays

Bombarded tumor specimens an cells were cultivated in appropriate growth media for 16 to 24 hrs. The tissues and cells were harvested by trypsinization and pelleted by centrifugation. Cells were lysed and extracted with appropriate buffer solutions. Tissue extracts were assayed for reporter gene expression 1 to 5 days after transduction. The level of reporter gene expression was then determined. Lux, CAT and beta-galactosidase enzyme activities were assayed as reported by Yang, et al (Proc. Natl. Acad. Sci. USA 87:9568, 1990). A standard luciferase determination was performed as follows: A 50 μl aliquot of tissue extract was added to a 450 μl reaction mixture containing Tris-Glycylglycine buffer (pH 7.8), $MgCl_2$, BSA ATP and the substrate, luciferin (200 mM). The light emission at relative light units (RLU) was measured digitally with a luminometer (Monolight, Model 2001.)

E. Analysis of Staging Gene's Affect on Reporter Gene Expression

The level of CMV-lux gene expression, at greater than 24 hrs after blasting, was compared between tissue samples transduced with the CMV-lux plasmid (sample A) and cells transduced with the staging gene, ras, and the CMV-lux plasmid (sample B). Significant increases (e.g., >150%) of lux expression in sample B over sample A illustrated the potential of activating ras oncogene in the sample B cells. Such ability to activate the ras oncogene or lack of it in a specific tumor represented the functional presence or absence of specific factor(s) or other "early" oncogene(s) (e.g. APC gene) in this test tumor. This situation indicated that the cells have progressed to the point of having all the components necessary to activate the ras gene. A result where the reporter gene expression of sample A approximately equaled that of sample B indicated the absence of the potential for activating the ras oncogene in these cells. Therefore, the cells had not progressed to this stage.

Triplicate samples of each cell line or primary cultures were analyzed for all experiments described herein.

2. SPECIFIC CELLS TESTED

A. MCF-7, CHO and NIH 3T3 Cells

We assayed MCF-7 cells, CHO cells and NIH 3T3 cells by the method of the present invention. MCF-7 cells are a human mammary malignant metastatic carcinoma cell line. CHO (Chinese Hamster ovary) cells and NIH 3T3 cells are immortalized (routine proliferation and increased growth rate) but are not known to be malignant or metastatic carcinoma cells. The results are summarized in Table 1 and Table 2.

TABLE 1

| Gene Transfer Vector | Luciferase Activity/Culture (RLU × $10^{-2}$) | | |
|---|---|---|---|
| | CHO cells | 3T3 cells | MCF-7 cells |
| CMV-Lux | 103,701 ± 51,000 | 52,867 ± 4,800 | 164,914 ± 43,000 |
| CMV-Lux + JR-ras | 281,045 ± 71,000 | 194,955 ± 41,000 | 329,604 ± 12,000 |
| CMV-Lux + p53 | 109,573 ± 21,000 | 26,879 ± 6,500 | 246,416 ± 45,000 |

TABLE 2

| +Staging Gene / −Staging Gene | (B)/(A) | Expression Activity Ratio | | |
|---|---|---|---|---|
| | | CHO | 3T3 | MCF-7 |
| (CMV-Lux + JRas) / CMV-Lux | | 2.7 | 3.7 | 1.99 |

TABLE 2-continued

| +Staging Gene / −Staging Gene | (B)/(A) | Expression Activity Ratio | | |
|---|---|---|---|---|
| | | CHO | 3T3 | MCF-7 |
| (CMV-Lux + p53) / CMV-Lux | | 1.05 | 0.51 | 1.50 |

These results indicate that the CHO and NIH 3T3 cells (which have B/A ratios of 2.7 an 3.7 for the ras experiment) have progressed in their tumorigenesis to the point of enabling the ras gene to modify cellular transcription and translation. The B/A ratio for the p53 gene experiments with these cells is 1.05 and .51, indicating that the CHO and 3T3 cells have not progressed to the p53 gene stage.

The situation with the MCF-7 cells is quite different. The B/A ratio is over 1.5 for both the p53 and ras experiments, indicating that the MCF-7 cells have progressed in tumorigenesis past the stages of the CHO and 3T3 cells. These results allow us to use the method of the present invention to distinguish between immortalized cells (e.g. benign tumors) and metastatic cancerous cells.

B. Normal Rat Mammary Epethelial Cells and NIH 3T3 Cells

Normal rat mammary epithelial cells (RMEC) and NIH 3T3 cells were compared. The results were as follows:

TABLE 3

| Gene Transfer Vector | Luciferase Activity (RLU)/μg protein | |
|---|---|---|
| | (RLU × $10^{-3}$) Normal RMEC | (RLU × $10^{-4}$) NIH 3T3 cells |
| CMV-Lux | 72.8 + 24 | 8.9 + 1 |
| CMV-Lux + JR-ras | 35.4 + 7 | 32 + 10 |

TABLE 4

| +Staging Gene / −Staging Gene | (B)/(A) | Expression Activity Ratio | |
|---|---|---|---|
| | | Normal RMEC | NIH 3T3 cells |
| (CMV-Lux + JRas) / CMV-Lux | | 0.48 | 3.59 |

NIH 3T3 cells had a similar response as in the previous experiment. The B/A ratio was >1.5, indicating that the cells have progressed to the ras stage of development. Normal rat mammary epithelial cells were used as a control. These cells demonstrated a repressed lux activity in cells transfected with CMV-ras and CMV-lux. The RMEC cells had a B/A ratio of less than 1, confirming their normal nature. Therefore, we are able to differentiate between normal, non-immortalized cells and immortalized cells. Because RMEC are mammary cells and responded appropriately in the assay, we think the assay is suitable for mammary tumor diagnosis.

We have performed experiments, similar to those described in Tables 3 and 4, designed to demonstrate the effect of different promoters and reporter genes. We attached the SV40 or the RSV promoters, instead of the CMV promoter, to the lux gene and cotransduced RMEC and NIH 3T3 cells with the lux gene and the JR-ras plasmid. The results were similar to those described in Table 4. The B/A ratio for the RMEC was <1 and the B/A ratio for the NIH 3T3 cells was >1.5. We also attached two different reporter genes, beta-galactosidase or CAT, to the CMV promoter and cotransduced RMEC and NIH 3T3 cells. The results again were ratios similar to those reported in Table 4. Thus, it is the employed staging gene, not the specific promoter or reporter genes we used, that is responsible for the observed effect.

C. HEP-G2 Cells

We analyzed HEP-G2 cells (human hepatic carcinoma cell line) by the method of the present invention by transduction with CMV-lux and CMV-ras. The results were as follows:

TABLE 5

| Transduction Vector | Lux Activity at 100 hrs after transduction (RLU × $10^{-2}$/culture) | Average |
| --- | --- | --- |
| 1. CMV-Lux (Sample A) | 24,455 | |
| 2. CMV-Lux (Sample A) | 59,972 | 42,213 |
| 3. CMV-Lux + CMV-ras (Sample B) | 76,571 | |
| 4. CMV-Lux + CMV-ras (Sample B) | 81,280 | 78,925 |

Thus, a >1.5 ratio of sample B/A was obtained for HEP-G2 liver carcinoma cells, confirming their development past the ras stage.

D. Normal Cells in Vivo

As a negative control, we cotransformed normal rat dermis skin tissue with CMV-Lux with or without CMV-ras. The cells that were not transfected with CMV-ras were transfected with JR-Gal. JR-Gal is a plasmid encoding beta-galactosidase, a reporter gene. The JR-Gal plasmid is used as a control to determine whether transduction using two plasmids, as opposed to one plasmid, has any affect on reporter gene expression.

Two month old Holtzman rats were anesthetized. The bottom skin (dermis) layers of abdominal tissues were surgically exposed (i.e. pulled away from muscle) and each rat was blasted on two sides, the left and the right dermis side. After blasting, the skin tissues were sutured back. The animals were allowed to recover under standard conditions. Three days later, the animal was sacrificed and the skin tissues recovered. The Lux activity in tissue extract was determined. The results were as follows. In three cases, the B/A ratio was less than 1.

TABLE 6

| | Skin Lux Activity in Relative Light Unit (RLU) | | |
| --- | --- | --- | --- |
| | Left Side (L) −Ras Vector: | Right Side (R) +Ras | |
| Rat No. | CMV-Lux + JR-Gal | CMV-Lux + JR-ras | B/A |
| #1 | 28,552 | 4,165 | 0.14 |
| #2 | 27,150 | 21,584 | 0.8 |

TABLE 6-continued

| | Skin Lux Activity in Relative Light Unit (RLU) | | |
| --- | --- | --- | --- |
| | Left Side (L) −Ras Vector: | Right Side (R) +Ras | |
| Rat No. | CMV-Lux + JR-Gal | CMV-Lux + JR-ras | B/A |
| #3 | 34,950 | 5,993 | 0.17 |
| #4 | 10,290 | 18,916 | 1.8 |

The average B/A ratio of the four rat experiments was 0.73, indicating a benign nature of the test samples. These experiments indicate that cotransduction with two plasmids, as opposed to one, is not responsible for changes in gene expression.

We claim:

1. A method for determining the stage of neoplastic development of cells comprising the steps of:
   (a) isolating cells;
   (b) dividing the cells into first and second samples;
   (c) transducing the cells of the first sample with a reporter gene;
   (d) transducing the cells of the second sample with both a reporter gene and a staging gene, the staging gene being the ras gene, wherein the ras staging gene is known to have a differential mode of expression in neoplastic and normal cells and wherein the staging gene is chosen by its ability to be predictive of a certain stage of neoplastic and normal cells and wherein the staging gene is chosen by its ability to be predictive of a certain stage of neoplastic development;
   (e) analyzing the first and second samples for the level of expression of the reporter gene; and
   (f) comparing the expression level of the reporter gene in the first and second samples to evaluate the stage of neoplastic development of the cells; wherein an expression level of the reporter gene in the second sample that is at least 1.5 times the expression level of the reporter gene in the first sample indicates that the neoplastic development of the cells has progressed at least to the stage of ras gene activation.

2. The method of claim 1 wherein the reporter gene is selected from the group consisting of lux, betagalactosidase, and CAT.

3. The method of claim 1 wherein the reporter gene is preceded by a promoter chosen from the group consisting of the SV40 promoter, the RSV promoter, and the CMV promoter.

4. The method of claim 1 wherein the cells are isolated from colon tissue.

5. The method of claim 1 wherein the cells are isolated from mammary tissue.

6. The method of claim 1 wherein the transducing of steps (c) and (d) comprises the bombarding of the first and second samples with DNA-coated carrier particles.

* * * * *